(12) United States Patent
Tanaka et al.

(10) Patent No.: US 9,103,065 B2
(45) Date of Patent: Aug. 11, 2015

(54) METHOD FOR PRODUCING HYDROPHILIC CELLULOSE FIBER

(75) Inventors: Chiaki Tanaka, Kyoto (JP); Yoshinari Yui, Kyoto (JP); Akira Isogai, Tokyo (JP)

(73) Assignee: GUNZE LIMITED, Kyoto (JP)

( * ) Notice: Subject to any disclaimer, the term of this patent is extended or adjusted under 35 U.S.C. 154(b) by 0 days.

(21) Appl. No.: 14/342,914

(22) PCT Filed: Sep. 11, 2012

(86) PCT No.: PCT/JP2012/073217
§ 371 (c)(1),
(2), (4) Date: Mar. 5, 2014

(87) PCT Pub. No.: WO2013/039070
PCT Pub. Date: Mar. 21, 2013

(65) Prior Publication Data
US 2014/0249305 A1   Sep. 4, 2014

(30) Foreign Application Priority Data
Sep. 12, 2011   (JP) ................................ 2011-198763

(51) Int. Cl.
| *C08B 15/04* | (2006.01) |
| *D06M 11/13* | (2006.01) |
| *D06M 11/30* | (2006.01) |
| *D06M 13/355* | (2006.01) |
| *D06M 11/01* | (2006.01) |
| *D06M 11/34* | (2006.01) |
| *D06M 11/50* | (2006.01) |
| *D06M 11/54* | (2006.01) |
| *D06M 13/388* | (2006.01) |
| *A61L 15/44* | (2006.01) |
| *C08L 1/02* | (2006.01) |
| *A61L 15/28* | (2006.01) |
| *D06M 101/06* | (2006.01) |

(52) U.S. Cl.
CPC ................ *D06M 11/13* (2013.01); *A61L 15/28* (2013.01); *A61L 15/44* (2013.01); *C08B 15/04* (2013.01); *C08L 1/02* (2013.01); *D06M 11/01* (2013.01); *D06M 11/30* (2013.01); *D06M 11/34* (2013.01); *D06M 11/50* (2013.01); *D06M 11/54* (2013.01); *D06M 13/355* (2013.01); *D06M 13/388* (2013.01); *A61L 2400/04* (2013.01); *D06M 2101/06* (2013.01)

(58) Field of Classification Search
CPC .............................. C08B 15/04; A61L 15/28
See application file for complete search history.

(56) References Cited

U.S. PATENT DOCUMENTS

| 2002/0098317 | A1* | 7/2002 | Jaschinski et al. .............. 428/72 |
| 2012/0065389 | A1 | 3/2012 | Miyawaki et al. |
| 2012/0130064 | A1 | 5/2012 | Isogai et al. |
| 2013/0296544 | A1 | 11/2013 | Isogai et al. |

FOREIGN PATENT DOCUMENTS

| JP | 56-079787 | 6/1981 |
| JP | 2001-131867 | 5/2001 |
| WO | 01/29309 | 4/2001 |
| WO | 2009/107637 | 9/2009 |
| WO | 2010/116794 | 10/2010 |
| WO | 2011/024807 | 3/2011 |
| WO | 2012/102153 | 8/2012 |

OTHER PUBLICATIONS

Mao et al., Ind. Eng. Chem. Res., 2010, 49, p. 113-116, Published on Web Nov. 16, 2009.*

* cited by examiner

*Primary Examiner* — Jonathan S Lau
(74) *Attorney, Agent, or Firm* — Hamre, Schumann, Mueller & Larson, P.C.

(57) ABSTRACT

The present invention provides a hydrophilized cellulose fiber producing method, comprising oxidizing cellulose fibers in a reaction solution containing a N-oxyl compound, an oxidizing agent, and a co-catalyst and oxidizing other cellulose fibers using the reaction solution again. The present invention relates to a hydrophilized cellulose fiber producing method, comprising the steps of: (1a) oxidizing cellulose fibers in a reaction solution containing a N-oxyl compound, an oxidizing agent, and sodium sulfate to provide oxidized cellulose fibers; and (1b) separating the obtained oxidized cellulose fibers from the reaction solution, and then adding other additional cellulose fibers and oxidizing agent to the reaction solution to oxidize the cellulose fibers again to provide oxidized cellulose fibers.

15 Claims, 2 Drawing Sheets

METHOD FOR PRODUCING HYDROPHILIC CELLULOSE FIBER

TECHNICAL FIELD

The present invention relates to a hydrophilized cellulose fiber producing method. Specifically, the present invention relates to a method of producing hydrophilized cellulose fibers by oxidizing a part of hydroxy groups in the cellulose fibers to carboxy groups.

BACKGROUND ART

Cotton garments (cellulose fiber products) such as underwear have been required to have high moisture-absorption properties and high moisture-desorption properties. Such a cotton garment (cellulose fiber product) with high moisture-absorption properties and high moisture-desorption properties may be obtained by, for example, hydrophilizing cellulose fibers used as raw materials. Various methods for hydrophilizing cellulose fibers are known, and one representative example of such methods is oxidizing a hydroxy group in cellulose to a carboxy group.

A known method of oxidizing a hydroxy group in cellulose to a carboxy group is oxidizing cellulose fibers used as raw materials in a reaction solution containing a N-oxyl compound such as 2,2,6,6-tetramethylpiperidine-N-oxyl (TEMPO) and a halogen-based oxidizing agent in the presence of a co-catalyst (see Patent Literature 1, for example).

For industrial oxidation and hydrophilization of cellulose fibers, it is desirable to reuse the reaction solution for the oxidation treatment. However, if a reaction solution is reused in oxidation of cellulose fibers with a N-oxyl compound and a halogen-based oxidizing agent, a halogen-based salt, which is a by-product of the reaction, inhibits the reaction. Thus, with a used reaction solution, it is typically difficult to introduce carboxy groups to cellulose fibers with sufficient efficiency.

CITATION LIST

Patent Literature

Patent Literature 1: WO 2011/024807

SUMMARY OF INVENTION

Technical Problem

As mentioned above, if a used reaction solution is reused in an oxidation step in which carboxy groups are introduced to cellulose fibers using a reaction solution containing a N-oxyl compound, an oxidizing agent, and a co-catalyst, the reaction efficiency is reduced. Thus, reuse of the reaction solution has not been considered as an effective way.

The present inventors have found that, in contrast to the above consideration, use of sodium sulfate as a co-catalyst enables reuse of the reaction solution for the oxidation treatment. The present inventors also have found that the amount of carboxy groups introduced to hydrophilized cellulose fibers is larger in an oxidation treatment performed using a used reaction solution than in an oxidation treatment performed using the initial reaction solution.

Based on the above findings, the present invention aims to provide a hydrophilized cellulose fiber producing method, comprising the steps of oxidizing cellulose fibers in a reaction solution containing a N-oxyl compound, an oxidizing agent, and a co-catalyst and oxidizing other cellulose fibers by reusing the reaction solution.

Solution to Problem

The present inventors have made keen studies to solve the above problems and have found that, in the hydrophilized cellulose fiber producing method comprising the step of oxidizing cellulose fibers in a reaction solution containing a N-oxyl compound, an oxidizing agent, and a co-catalyst and oxidizing other cellulose fibers using the reaction solution again, use of sodium sulfate as a co-catalyst is effective in improving the efficiency of the reaction that introduces carboxy groups into hydroxy groups. The present invention is thus completed based on the findings.

Item 1. A hydrophilized cellulose fiber producing method, comprising the steps of: (1a) oxidizing cellulose fibers in a reaction solution containing a N-oxyl compound, an oxidizing agent, and sodium sulfate to provide oxidized cellulose fibers; and (1b) separating the obtained oxidized cellulose fibers from the reaction solution, and then adding other additional cellulose fibers and oxidizing agent to the reaction solution to oxidize the cellulose fibers again to provide oxidized cellulose fibers.

Item 2. The method according to item 1, wherein the N-oxyl compound used in step (1a) is 2,2,6,6-tetramethylpiperidine-N-oxyl.

Item 3. The method according to item 1 or 2, wherein the cellulose fibers used in step (1a) are rayon fibers.

Item 4. The method according to item 1, wherein step (1b) is performed twice or more.

Item 5. The method according to item 1 or 2, wherein the oxidizing agent used in step (1a) and/or step (1b) is a halogen acid oxidizing agent.

Item 6. The method according to item 3, wherein the halogen acid oxidizing agent used in step (1a) and/or step (1b) is a hypohalous acid, a halogenated isocyanuric acid, or a salt thereof.

Item 7. The method according to any one of items 1 to 4, further comprising step (2) of oxidizing the oxidized cellulose fibers obtained in steps (1a) and (1b) in a reaction solution containing an oxidizing agent.

Item 8. The method according to item 5, wherein the oxidizing agent used in step (2) is a halogen acid oxidizing agent.

Item 9. The method according to item 6, wherein the halogen acid oxidizing agent used in step (2) is a halous acid or a salt thereof.

Item 10. The method according to any one of items 5 to 7, further comprising step (3) of dehalogenating the oxidized cellulose fibers obtained in step (2) with a dehalogenating agent.

Item 11. The method according to any one of items 5 to 7, further comprising step (4a) of reducing the oxidized cellulose fibers obtained in step (2) in a reaction solution containing a reducing agent.

Item 12. The method according to item 8, further comprising step (4b) of reducing the oxidized cellulose fibers obtained in step (3) in a reaction solution containing a reducing agent.

Item 13. The method according to any one of items 5 to 7, further comprising the step of mixing the oxidized cellulose fibers obtained in step (2) with a dehalogenating agent and a reducing agent to perform a dehalogenation treatment to remove halogens remaining in the oxidized cellulose fibers simultaneously with a reduction treatment to reduce ketone group(s) in the 2- and/or 3-position(s) of a glucose unit in the oxidized cellulose fibers.

Item 14. The method according to item 8 or 11, wherein the dehalogenating agent is at least one selected from the group consisting of hydrogen peroxide and ozone.

Item 15. The method according to any one of items 9 to 12, wherein the reducing agent is at least one selected from the group consisting of thiourea, hydrosulfite, sodium bisulfite, sodium borohydride, sodium cyanoborohydride, and lithium borohydride.

Item 16. A method of reusing a reaction solution, comprising the steps of: oxidizing cellulose fibers in a reaction solution containing a N-oxyl compound, an oxidizing agent, and sodium sulfate to provide oxidized cellulose fibers; and separating the oxidized cellulose fibers from the reaction solution used in the oxidizing step, and then adding additional other cellulose fibers and oxidizing agent in the reaction solution to oxidize the cellulose fibers again.

Item 17. Hydrophilized cellulose fibers obtained by the method according to any one of items 1 to 15.

Item 18. A hemostatic material comprising the hydrophilized cellulose fibers according to item 17.

Advantageous Effects of Invention

According to the hydrophilized cellulose fiber producing method of the present invention, if a reaction solution used in a step of oxidizing cellulose fibers with a N-oxyl compound and an oxidizing agent in the presence of sodium sulfate is reused in another oxidation step, the amount of carboxy groups introduced to the cellulose fibers increases as compared with that in the initial oxidation treatment of cellulose fibers. This allows improvement in the reaction efficiency of the carboxy groups.

In addition, reuse of the reaction solution used in the oxidizing treatment eliminates the need for disposing the N-oxyl compound used as a catalyst or sodium sulfate used as a co-catalyst. Reuse of the reaction solution is therefore useful from an economic viewpoint.

DESCRIPTION OF EMBODIMENT

Figure 1:
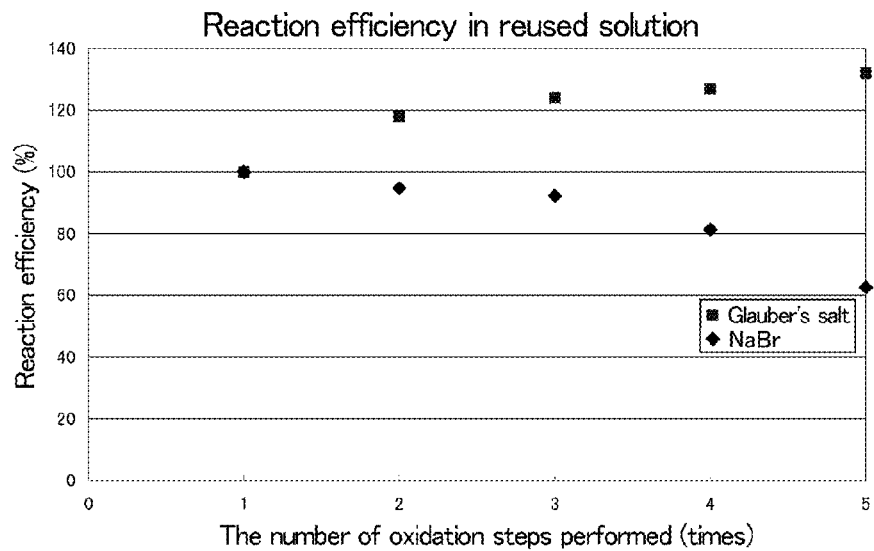
FIG. 1 is a graph plotting the relation between the number of oxidation steps performed and reaction efficiency.

In the following, the hydrophilized cellulose fiber producing method of the present invention is described in detail.
Step (1a)

In step (1a), cellulose fibers are oxidized in a reaction solution containing a N-oxyl compound, an oxidizing agent, and sodium sulfate. That is, a COOH group is introduced to the 6-position in cellulose fibers to provide oxidized cellulose fibers.

Material cellulose fibers usable in the hydrophilized cellulose fiber producing method of the present invention may be natural cellulose fibers from vegetables, animals, or gels produced by bacteria, or may be regenerated cellulose fibers. Specifically, natural cellulose fibers such as cotton, hemp, pulp, and bacterial cellulose, regenerated cellulose fibers such as rayons and cupro, and the like may be used.

Examples of the rayon include viscose rayon, cuprammonium rayon, and polynosic rayon.

The form of the material cellulose fibers is not limited to a fabric form (e.g., woven and knitted fabric form, a non-woven fabric form). The material cellulose fibers may be in the form of a yarn such as a filament, a staple, and a string. The fibers may have a structure of combined filament, mixed spun, union fabric, mixed woven, or mixed knitted.

The material cellulose fibers are preferably previously water-washed and refined for sufficient hydrophilization of cellulose fibers in the subsequent steps and for sufficient bleaching effect. "Refine" herein means a treatment for removing impurities in natural fibers, oil solutions used in spinning and knitting steps, and machine oils, iron mold, and the like attached to the fibers during the processing steps.

In the step of oxidizing cellulose fibers with a N-oxyl compound and an oxidizing agent in the presence of a co-catalyst, the oxidizing agent (e.g., a halogen-based oxidizing agent) is consumed and thereby a salt is produced as a by-product. The salt inhibits the reaction of the co-catalyst used in the oxidizing step. Therefore, it is known that reuse of the reaction solution used in the oxidizing step reduces the reaction efficiency.

In the present invention, sodium sulfate is added to the reaction solution as a co-catalyst in the oxidation treatment of step (1a). This suppresses the reduction in the reaction efficiency caused by the by-product salt, enabling reuse of the reaction solution in the oxidation treatment of step (1b) described below.

The sodium sulfate used in step (1a) may be in the form of an anhydride or a hydrate. Examples of the sodium sulfate hydrate include sodium sulfate decahydrate (Glauber's salt). In step (1a), the sodium sulfate content in the reaction solution is preferably about 0.1 to about 200 g/L, more preferably about 0.33 to about 100 g/L, even more preferably about 3.3 to about 33.3 g/L, and particularly preferably about 4.5 to about 10 g/L. If the sodium sulfate content is set to about 0.1 g/L or more, an increased amount of COOH groups tend to be introduced to the cellulose fibers, and the effect of decreasing bending resistance is provided. If the sodium sulfate content is set to about 200 g/L or less, reduction in polymerization degree of the cellulose fibers is suppressed, allowing the TEMPO oxidation reaction to efficiently progress.

Figure 2:
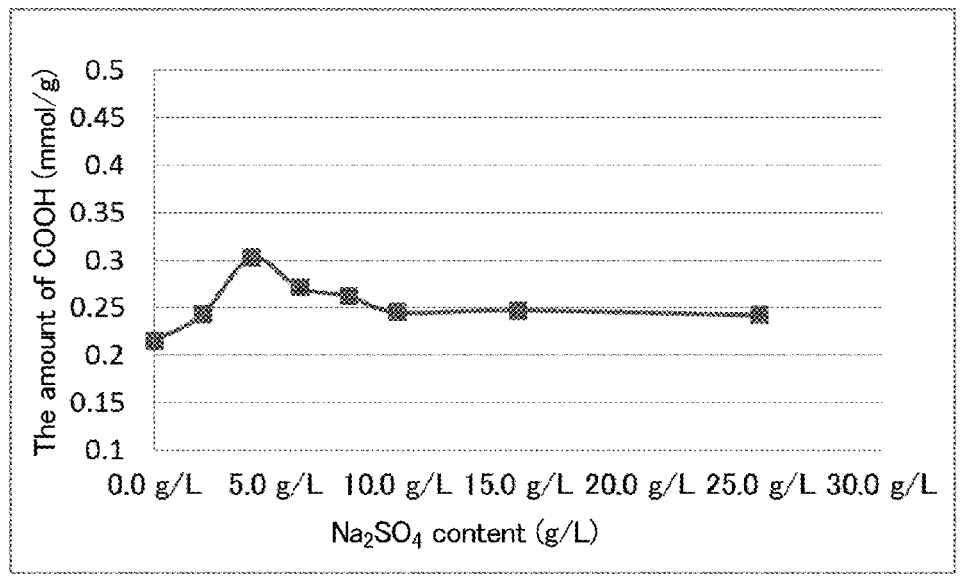
FIG. 2 is a graph showing one example of the relation between sodium sulfate content and the amount of COOH groups introduced to cellulose fibers.

One example of the relation between the sodium sulfate content and the amount of COOH groups introduced to cellulose fibers is shown in FIG. 2.

The sodium sulfate content in the reaction solution is preferably about 0.1 to about 600% owf, more preferably about 1 to about 300% owf, and even more preferably about 10 to about 100% owf. If the sodium sulfate content is set to 0.1% owf or more, an increased amount of COOH groups tend to be introduced to the cellulose fibers, and the effect of decreasing bending resistance is provided. If the sodium sulfate content is set to about 600% owf or less, reduction in polymerization degree of the cellulose fibers is suppressed, allowing the TEMPO oxidation reaction to efficiently progress.

The unit "% owf" means % by weight based on weight of fibers. The same shall apply hereinafter.

The N-oxyl compound in the reaction solution is used as a catalyst in the oxidation of the cellulose fibers. Specific examples of the N-oxyl compound include a compound represented by Formula (I), a compound represented by Formula (II), and the like.

[Chem. 1]

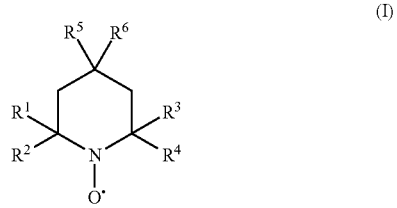

In Formula (I), $R^1$ to $R^4$ are the same as or different from one another, each representing a lower alkyl group having about 1 to 4 carbon atoms. $R^5$ and $R^6$ are the same as or different form each other, each representing a hydrogen atom; an acetylamino group; a carboxy group; a phosphonooxy group; an amino group; 2-halogenated acetylamino group substituted with a halogen atom (a fluorine atom, a chlorine atom, a bromine atom, or an iodine atom); a hydroxy group; a lower alkoxy group having about 1 to 4 carbon atoms; or an adamantane group. $R^5$ and $R^6$ may be bonded to each other through an oxygen atom to form an oxo group.

[Chem. 2]

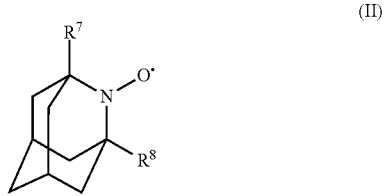

In Formula (II), $R^7$ and $R^8$ are the same as or different from each other, each representing a hydrogen atom or a lower alkyl group having about 1 to 4 carbon atoms.

Specific examples of the N-oxyl compound include 2,2,6, 6-tetramethylpiperidine-N-oxyl (TEMPO), TEMPO derivatives having a functional group in carbon at 4-position of TEMPO, 2-azaadamantane-N-oxyl, and the like.

Specific examples of the TEMPO derivative include 4-acetamido TEMPO, 4-carboxy TEMPO, 4-phosphonooxy TEMPO, 4-amino-TEMPO, 4-(2-bromoacetamido)-TEMPO, 4-hydroxy TEMPO, 4-oxy TEMPO, 4-methoxy TEMPO, and the like.

Preferred among these N-oxyl compounds are TEMPO, 4-methoxy TEMPO, and 4-acetamido TEMPO because these compounds rapidly react with and oxidize carbon at 6-position in each glucose unit in the cellulose fibers.

It is sufficient that the N-oxyl compound is used in a catalytic amount. Specifically, the amount of N-oxyl compound in the reaction solution is preferably about 0.01 to about 3 g/L. Since the amount of N-oxyl compound does not significantly affect the degree of the hydrophilizing treatment or the quality of the resulting cellulose fibers, an amount of about 0.1 to about 2 g/L is economical and more preferred.

Also, the amount of N-oxyl compound is preferably about 0.03 to about 9.0% owf, and more preferably about 0.75 to about 6.0% owf.

The oxidizing agent contained in the reaction solution in step (1a) is preferably a halogen acid-based oxidizing agent, and more preferably a hypohalous acid, a halogenated isocyanuric acid, or a salt thereof.

Examples of the halogen in the hypohalous acid include chlorine, bromine, and iodine. Specific examples of the hypohalous acid include hypochlorous acid, hypobromous acid, and hypoiodous acid.

The metal salt forming the hypohalite may be, for example, an alkali metal salt such as lithium, potassium, and sodium salts; alkali earth metal salt such as calcium, magnesium, and strontium salts, and the like. The metal salt may also be a salt of ammonium and a hypohalous acid.

Specific examples of the hypohalite in the case that the hypohalous acid is a hypochlorous acid include lithium hypochlorite, potassium hypochlorite, sodium hypochlorite, calcium hypochlorite, magnesium hypochlorite, strontium hypochlorite, ammonium hypochlorite, and the like. Also, hypobromous acid salts and hypoiodous acid salts corresponding to these hypochlorous acid salts can be used.

The halogenated isocyanuric acid or salt thereof may be a halogenated isocyanuric acid represented by Formula (III) or a salt thereof.

[Chem. 3]

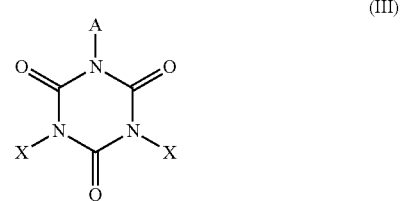

In Formula (III), A represents a hydrogen atom; a halogen atom such as a fluorine atom, a chlorine atom, a bromine atom, and an iodine atom; an alkali metal, or an alkali earth metal. Xs are the same as or different from each other, each representing a halogen atom such as a fluorine atom, a chlorine atom, a bromine atom, and an iodine atom.

Examples of the alkali metal forming the salt of the halogenated isocyanuric acid include lithium, potassium, and sodium. Examples of the alkali earth metal forming the salts of the halogenated isocyanuric acid include calcium, magnesium, and strontium. Salts of ammonium and halogenated isocyanuric acids may be used. Each of the salts of halogenated isocyanuric acids may be in the form of a hydrate.

Specific examples of the halogenated isocyanuric acid include dichloroisocyanuric acid, trichloroisocyanuric acid, and the like. Examples of the salt of the halogenated isocyanuric acid include sodium dichloroisocyanurate and the like.

If the oxidizing agent in step (1a) is an alkali metal hypohalite, alkali metal hypochlorites (e.g. sodium hypochlorite) are preferred. If the oxidizing agent is a halogenated isocyanuric acid, sodium dichloroisocyanurate and sodium dichloroisocyanurate dihydrate are preferred because these are highly soluble in water and excellent in bleaching and antiseptic effects in water.

The oxidizing agent content in the reaction solution is preferably about 0.03 to about 10 g/L, and more preferably about 1.0 to about 5.0 g/L. If the oxidizing agent content is set to about 0.03 g/L or more, the effect of improving hydrophilization of the cellulose fibers and the effect of bleaching the cellulose fibers are provided. If the oxidizing agent content is set to about 10 g/L or less, the effect of preventing a reduction in the polymerization degree and in feel is provided.

The oxidizing agent content is also preferably about 0.1 to about 30% owf, and more preferably about 3.0 to about 15% owf.

The pH of the reaction solution in step (1a) is preferably held at about 4 to about 12, and more preferably held at about 8 to about 11. A pH within this range is suitable for an oxidized N-oxyl compound to act on the cellulose fibers.

The pH of the reaction solution may be controlled by appropriately adding a basic substance (e.g., ammonia, potassium hydroxide, sodium hydroxide) or an acidic substance (e.g., organic acids such as acetic acid, oxalic acid, succinic acid, glycol acid, malic acid, citric acid, and benzoic acid; inorganic acids such as nitric acid, hydrochloric acid, sulfuric acid, and phosphoric acid).

The reaction solution used in step (1a) may further contain a penetrating agent. Examples of the penetrating agent include known penetrating agents used for cellulose fibers. Specific examples thereof include anionic surfactants (e.g., carboxylates, sulfates, sulfonates, phosphates) and non-ionic surfactants (e.g., polyethyleneglycol-based surfactants, multiple alcohol-based surfactants). For example, Shintol (a product name, produced by Takamatsu Oil & Fat Co., Ltd.) may be used.

The penetrating agent added to the reaction solution allows chemical agents to penetrate to the inside of the cellulose fibers, which enables introduction of a larger amount of carboxy groups (aldehyde groups) into the surface of the cellulose fibers. This improves hydrophilic properties (moisture-absorption properties) of the cellulose fibers.

The solvent of the reaction solution in step (1a) is water.

In step (1a), the method of oxidizing the cellulose fibers is not particularly limited. Preferably, a N-oxyl compound and a co-catalyst are added to a reaction solvent, then cellulose fibers are immersed into the solvent, and thereafter an oxidizing agent is added. Oxidation of cellulose fibers by such a method allows the N-oxyl compound and the co-catalyst to penetrate the cellulose fibers, which enables hydrophilization without uneven processing.

In step (1a), the reaction solution is preferably used in a bath ratio of about 10 to about 100 g per gram of the cellulose fibers, and more preferably in a bath ratio of about 15 to about 30 g per gram of the cellulose fibers. If the reaction solution is used in a bath ratio of about 10 g or more per gram of the cellulose, the effect of improving contacting efficiency of the cellulose fibers and the reaction solution is provided. If the reaction solution is used in a bath ratio of about 100 g or less per gram of the cellulose fibers, the effect of maintaining contacting efficiency of the cellulose fibers and the reaction solution is provided.

The oxidation treatment temperature in step (1a) is preferably about 0° C. or higher, and more preferably about 20° C. or higher because such a temperature enables introduction of a sufficient amount of COOH groups to the cellulose fibers, prevention of transpiration of the oxidizing agent, and retention of effective halogens in the oxidation treatment. The oxidation treatment temperature in step (1a) is also preferably about 50° C. or less, and more preferably about 30° C. or less because such a temperature prevents reduction in the polymerization degree of the cellulose fibers and embrittlement of the cellulose fibers.

The oxidation treatment time in step (1a) is preferably about 1 minute or longer, and more preferably about 3 minutes or longer because such an oxidation treatment time enables introduction of sufficient amount of COOH groups to the cellulose fibers and it takes some time before the cycle of the reaction starts. The oxidation treatment time in step (1a) is also preferably about 30 minutes or shorter, and more preferably 15 minutes or shorter because such an oxidation treatment time prevents a reduction in the polymerization degree of the cellulose fibers and embrittlement of the cellulose fibers.

Step (1b)

In step (1b), oxidized cellulose fibers are separated from the reaction solution, and other additional cellulose fibers and oxidizing agent are added to the reaction solution to oxidize the cellulose fibers again.

That is, step (1b) is a step of oxidizing cellulose fibers by reusing the reaction solution used in step (1a).

Specific examples of cellulose fibers used in step (1b) include fibers listed above.

Any of the oxidizing agents listed above may be used as the oxidizing agent added in step (1b). Specifically, halogen acid-based oxidizing agents are preferred, and hypohalous acids, halogenated isocyanuric acids, and salts thereof are more preferred. More specific examples of the oxidizing agent include alkali metal hypohalites, sodium dichloroisocyanurate, and sodium dichloroisocyanurate dihydrate.

The oxidizing agent content in the reaction solution in step (1b) is preferably about 0.03 to about 10 g/L and more preferably about 1.0 to about 5.0 g/L. If the oxidizing agent content is set to about 0.03 g/L or more, the effect of improving hydrophilization of the cellulose fibers and the effect of bleaching the cellulose fibers are provided. If the oxidizing agent content is set to about 10 g/L or less, the effect of preventing reduction in the polymerization degree and in feel is provided.

The oxidizing agent content is also preferably about 0.1 to about 30% owf, and more preferably about 3.0 to about 15% owf.

The pH of the reaction solution in step (1b) is preferably held at about 4 to about 12, and more preferably held at about 8 to about 11, as in step (1a). A pH within this range is suitable for an oxidized N-oxyl compound to act on the cellulose fibers.

If the pH of the reaction solution used in step (1b) is out of the above range, the pH may be adjusted by appropriately adding, to the reaction solution, a basic substance (e.g., ammonia, potassium hydroxide, sodium hydroxide) or an acidic substance (e.g., organic acids such as acetic acid, oxalic acid, succinic acid, glycol acid, malic acid, citric acid, and benzoic acid; inorganic acids such as nitric acid, hydrochloric acid, sulfuric acid, and phosphoric acid).

The reaction solution used in step (1b) may further contain a penetrating agent. Any of the penetrating agents listed above may be used.

In step (1b), the reaction solution is preferably used in a bath ratio of about 10 to about 100 g per gram of the cellulose fibers, and more preferably in the bath ratio of about 15 to about 30 g per gram of the cellulose fibers. If the reaction solution is used in a bath ratio of about 10 g or more per gram of the cellulose, the effect of improving contacting efficiency of the cellulose fibers and the reaction solution is provided. If the reaction solution is used in a bath ratio of about 100 g or less per gram of the cellulose fibers, the effect of maintaining contacting efficiency of the cellulose fibers and the reaction solution is provided.

The reaction solvent, the oxidation treatment temperature, and the oxidation treatment time are approximately the same as those in step (1a).

The oxidation treatment of step (1b) is performed at least once. Performing the treatment twice or more improves the efficiency of the oxidizing reaction of the cellulose fibers, and therefore is preferred from an economic viewpoint.

The upper limit of the number of times that the oxidation treatment of step (1b) is performed is not particularly limited, and preferably five times or less from the viewpoint of the reaction efficiency and control of catalyst concentration and co-catalyst concentration.

After the completion of the oxidation treatment of step (1b), a treatment is preferably performed if necessary for removing unreacted oxidizing agent (e.g., hypohalous acid or salts thereof, halogenated isocyanuric acid or salts thereof, hypohalous acid or salts thereof produced through decomposition of halogenated isocyanuric acid or salts thereof). Thereafter, the obtained fibers are preferably repeatedly water-washed.

Step (2)

In step (2), the oxidized cellulose fibers obtained in steps (1a) and (1b) are oxidized in a reaction solution containing an oxidizing agent to oxidize an aldehyde group present in the oxidized cellulose fibers obtained in steps (1a) and (1b).

By the oxidation treatments of steps (1a) and (1b), primary hydroxy groups of the glucose units on the microfibril surface of the cellulose fibers are selectively oxidized to carboxy groups. However, some aldehyde groups are produced in addition to the carboxy groups. The aldehyde group produced causes beta elimination or coloring during heating, resulting in low-molecule cellulose fibers having reduced strength.

Step (2) is a step of oxidizing aldehyde groups produced in steps (1a) and (1b) to carboxy groups in order to provide oxidized cellulose fibers free from aldehyde groups.

The materials used in step (2) are the oxidized cellulose fibers obtained in step (1b).

The oxidizing agent usable in step (2) is one capable of oxidizing an aldehyde group to a carboxy group. Specific examples thereof include halous acids or salts thereof (e.g., chlorous acid or salts thereof, bromous acid or salts thereof, iodous acid or salts thereof) and peracids (e.g., hydrogen peroxide, peracetic acid, persulfuric acid, perbenzoic acid). These oxidizing agents may be used alone, or may be used in combination of two or more thereof. These may also be used in combination of an oxidase such as laccase. The oxidizing agent content may be appropriately set, and is preferably in the range of 0.01 to 50 mmol/g based on the cellulose fibers.

The halogen in the halous acid salt may be chlorine, bromine, iodine, or the like. Examples of the salt forming the halous acid salt include alkali metal salts such as lithium, potassium, and sodium salts; alkali earth metal salts such as calcium, magnesium, and strontium salts; and ammonium salts. More specific examples of the halous acid salt in the case that the halous acid is chlorous acid include lithium chlorite, potassium chlorite, sodium chlorite, calcium chlorite, magnesium chlorite, strontium chlorite, and ammonium chlorite. Also, bromous acid salts or iodous acid salts corresponding to these chlorous acid salts may be used.

Preferable oxidizing agents in step (2) include alkali metal salts of halous acid, and alkali metal chlorites are more preferred.

The oxidizing agent content in the reaction solution is preferably about 1 to about 90 g/L, and more preferably about 2 to about 20 g/L. If the oxidizing agent content is set to about 1 g/L or more, the effect of bleaching the cellulose fibers is provided in addition to the oxidizing effect of the aldehyde group. If the oxidizing agent content is set to about 90 g/L or less, the effect of preventing embrittlement of cellulose fibers caused by chlorine in the oxidizing agent is provided.

The oxidizing agent content is preferably about 2 to about 180% owf, and more preferably about 4 to about 40% owf.

The pH of the reaction solution in the oxidation treatment in step (2) is preferably maintained at neutral or acidic. More specifically, the pH is preferably in the range of 3 to 7. In particular, care should be taken so that the pH of the reaction solution should not be 8 or greater. If the pH is within this range, the aldehyde groups can be oxidized to carboxy groups while preventing beta elimination caused by the aldehyde group in carbon at 6-position in cellulose produced in steps (1a) and (1b), enabling hydrophilization of the cellulose fibers without reducing the strength.

Preferably, a buffer solution is further added to the reaction solution. Examples of usable buffer solution include phosphoric acid buffer solutions, acetic acid buffer solutions, citric acid buffer solutions, boric acid buffer solutions, tartaric acid buffer solutions, tris buffer solutions, and the like.

The buffer solution suppresses changes in pH of the reaction solution, which eliminates a need for continuous addition of an acid or alkali to maintain pH.

In step (2), the reaction solution is preferably used in a bath ratio of about 5 to about 100 g per gram of the cellulose fibers, and more preferably in the bath ratio of about 10 to about 30 g per gram of the cellulose fibers. If the reaction solution is used in a bath ratio of about 5 g or more per gram of the cellulose, the effect of improving contacting efficiency of the cellulose fibers and the reaction solution is provided. If the reaction solution is used in a bath ratio of about 100 g or less per gram of the cellulose fibers, the effect of maintaining contacting efficiency of the cellulose fibers and the reaction solution is provided.

In the oxidation treatment in step (2), a chelating agent, a surfactant, a penetrating agent, and/or the like may be appropriately added in order to improve the effect of preventing embrittlement of the cellulose fibers caused by metals.

The oxidation treatment temperature in step (2) is preferably about 60° C. or higher, and more preferably about 70° C. or higher because such a temperature enables sufficient oxidation of the aldehyde groups in the oxidized cellulose fibers to COOH groups and allows the effect of bleaching the cellulose fibers to be exerted. The oxidation treatment temperature in step (2) is also preferably about 98° C. or less, and more preferably about 90° C. or less because such a temperature prevents a reduction in the polymerization degree of the cellulose fibers and embrittlement of the cellulose fibers caused by chlorine in the oxidizing agent.

The oxidation treatment time in step (2) is preferably about 30 minutes or longer, and more preferably about 50 minutes or longer because such an oxidation treatment time enables sufficient oxidation of the aldehyde group to a COOH group in the oxidized cellulose fibers and allows the effect of bleaching the cellulose fibers to be exerted. The oxidation treatment time in step (2) is preferably about 120 minutes of shorter, and more preferably 100 minutes or shorter because such a temperature prevents reduction in the polymerization degree of the cellulose fibers and embrittlement of the cellulose fibers caused by chlorine in the oxidizing agent.

Since the reaction container can be sealed in the oxidation treatment in step (2), a pressure device may be installed to pressurize the inside of the container in the oxidation treatment.

After the completion of the oxidation treatment in step (2), the oxidizing reaction is preferably appropriately terminated, and the resulting fibers are preferably repeatedly water-washed.

Step (3) (Dehalogenation Treatment)

In step (3), the oxidized cellulose fibers obtained in step (2) are dehalogenated.

The materials used in the dehalogenation treatment in step (3) are the oxidized cellulose fibers obtained in the oxidizing agent in step (2).

If a halogen-based oxidizing agent is used as the oxidizing agent in steps (1a), (1b), and (2), halogens derived from the oxidizing agent attach or bond to the resulting oxidized cellulose fibers.

Thus, it is preferred to perform a dehalogenation treatment to remove such halogens remaining in the oxidized cellulose fibers. The dehalogenation treatment is performed by immersing the oxidized cellulose fibers in a dehalogenation agent such as a hydrogen peroxide solution or an ozone solution.

The concentration of the dehalogenating agent in the reaction solution used in step (3) may be dependent on the kind of the dehalogenating agent, and is preferably about 0.1 to about 100 g/L, and more preferably about 0.67 to about 10 g/L in the reaction solution.

The dehalogenating agent content is preferably about 1 to about 300% owf, and more preferably about 2 to about 30% owf.

In the dehalogenation treatment in step (3), the reaction solution is preferably used in a bath ratio of about 5 to about 100 g per gram of the cellulose fibers, and more preferably in the bath ratio of about 5 to about 50 g per gram of the cellulose fibers. If the reaction solution is used in a bath ratio of about 5 g or more per gram of the cellulose, the effect of improving contacting efficiency of the cellulose fibers and the reaction and the effect of neutralizing the oxidizing agent remaining in the cellulose fibers are provided. If the reaction solution is used in a bath ratio of about 100 g or less per gram of the cellulose fibers, the contacting efficiency of the cellulose fibers and the reaction solution can be maintained, and the effect of neutralizing the oxidizing agent remaining in the cellulose fibers is provided.

The reaction solution used in the dehalogenating treatment in step (3) preferably has a pH of about 8 to about 11, and more preferably about 9.5 to about 10.7. If the pH of the reaction solution is set to about 8 or greater, the effect of neutralizing the oxidizing agent remaining in the cellulose fibers is provided. If the pH of the reaction solution is set to about 11 or smaller, the effect of preventing embrittlement of the cellulose fibers caused by a reaction on the alkaline-side is provided.

The dehalogenation treatment temperature in step (3) is preferably about 40° C. or higher and more preferably about 45° C. or higher from the viewpoint of producing a dechlorination effect. The dehalogenation treatment temperature in step (3) is also preferably about 90° C. or lower, and more preferably about 80° C. or lower from the viewpoint of preventing embrittlement of the cellulose fibers caused by a reaction on the alkaline-side and so on.

The dehalogenation treatment time in step (3) is preferably about 5 minutes or longer, and more preferably about 10 minutes or longer from the viewpoint of sufficient dehalogenation treatment and so on. The dehalogenation treatment time in step (3) is also preferably about 60 minutes or shorter, and more preferably 40 minutes or shorter because the oxidized cellulose fibers may be embrittled, hardened, and so on, if they are exposed to alkaline conditions for a long time.

Step (4) (Reduction Treatment)

Though a larger amount of carboxy groups can be introduced to the cellulose fiber surface in steps (1a), (1b) and (2) and the dehalogenation treatment of step (3), the oxidation treatments may cause yellowing (loss of whiteness). The treatments cause not only oxidation of carbon at 6-position in the cellulose fibers, but also oxidation of carbon at 2- or 3-position in some of the glucose units, producing a ketone. This ketone is presumably contributes to the yellowing. The reduction treatment with a reducing agent after the above steps can reduce the ketone produced and thereby inhibit yellowing (loss of whiteness) of the hydrophilized cellulose fibers.

The reduction treatment of step (4) is preferably performed after the dehalogenation treatment of step (3), if the dehalogenation treatment of step (3) is performed. If the dehalogenation treatment of step (3) is not performed, step (4) is performed after the oxidation treatment of step (2).

The reducing agent is one which is capable of reducing ketone groups produced in some of the glucose units to alcohol and does not reduce the carboxy groups produced. Specific examples thereof include thiourea, hydrosulfite, sodium bisulfite, sodium borohydride, sodium cyanoborohydride, and lithium borohydride. Preferred among these are sodium borohydride and sodium bisulfite because these are excellent in the initial whiteness and highly effective in preventing loss of whiteness.

Examples of the solvent of the reaction solution containing the reducing agent include ordinary water and any kind of water such as distilled water, ion-exchanged water, well water, and tap water. The reducing agent in the reaction solution preferably has a concentration of about 0.02 to about 4 g/L, and more preferably about 0.2 to about 2 g/L. If the concentration is set to be within the above range, the effect of suppressing embrittlement of the oxidized cellulose fibers caused by an excess oxidizing agent is provided.

The reducing agent content is preferably about 0.06 to about 12% owf, and more preferably about 0.6 to about 6.0% owf.

In the reduction treatment with the reducing agent, the reaction solution preferably has a pH of about 7 or greater, more preferably about 7.5 or greater, and even more preferably about 8 or greater because such a pH value is favorable in maintaining the activity of the reducing agent. Also, the reaction solution in the reduction treatment with the reducing agent preferably has a pH of about 12 or smaller, and more preferably about 11 or smaller because such a pH can suppress embrittlement of a fabric caused by the alkalinity. The pH of the reaction solution can be controlled by appropriately adding ammonia water, hydrochloric acid, calcined soda, NaOH, KOH, and the like.

In the reduction treatment, the reaction solution is preferably used in a bath ratio of about 5 to about 100 g per gram of the cellulose fibers, and more preferably in the bath ratio of about 5 to about 50 g per gram of the cellulose fibers. If the reaction solution is used in a bath ratio of about 5 g or more per gram of the cellulose fibers, the reaction solution favorably contact with the cellulose fibers, resulting in the effect of neutralizing chlorine. If the reaction solution is used in a bath ratio of about 50 g or less per gram of the cellulose fibers, the effect of maintaining stirring efficiency of the cellulose fibers and the reaction solution is provided.

The reaction temperature in the reduction treatment with a reducing agent is preferably, for example, about 10° C. to about 80° C., and more preferably about 20° C. to about 40° C. The temperature may be appropriately changed depending on the kind and the added amount of the reducing agent.

The dehalogenation treatment of step (3) and the reduction treatment of step (4) may be performed at the same time.

In the case of performing the dehalogenation treatment of step (3) and the reducing agent of step (4) at the same time, the kind of the dehalogenating agent and the reducing agent, the amount thereof, the bath ratio, and the reaction conditions are the same as those in steps (3) and (4).

In the hydrophilized cellulose fibers (oxidized cellulose fibers) obtained by the method of producing hydrophilized cellulose described above, at least part of the hydroxy groups located on the microfibril surface of the cellulose is oxidized only by carboxy groups. In particular, reuse of the reaction solution used in step (1a) in the oxidation treatment of step (1b) can improve the degree of substitution of carboxy groups.

The present invention also relates to a method of reusing a reaction solution, comprising the steps of: oxidizing cellulose fibers in a reaction solution containing a N-oxyl compound, an oxidizing agent, and sodium sulfate to provide oxidized cellulose fibers; and separating the oxidized cellulose fibers from the reaction solution used in the oxidizing step, and then adding other additional cellulose fibers and oxidizing agent to the reaction solution to oxidize the cellulose fiber again.

The reaction solution used in the oxidizing step may be the same as that used in the (1a).

Reuse of the reaction solution used in the oxidation treatment eliminates the need for disposing the N-oxyl compound used as a catalyst or sodium sulfate used as a co-catalyst. Therefore, reuse of the reaction solution is preferable from an economic viewpoint.

If cellulose fibers are oxidized using the used reaction solution again, the amount of carboxy groups introduced to the cellulose fibers is larger than that introduced to the cellulose fibers obtained in step (1a), improving the reaction efficiency.

The hydrophilized cellulose fibers obtained by the hydrophilized cellulose fiber producing method of the present invention are substantially free from cellulose fibers in which carbon at 6-position is replaced by an aldehyde group. Thus, a coloring component derived from the aldehyde groups is less likely to be produced through a heating treatment. The hydrophilized cellulose fibers obtained by the method are therefore suitably used in garment applications (e.g., underwear) requiring high whiteness. Also, since the quality does not deteriorate by heat, processing of the fibers is not limited, and thus the fibers are easy-to-handle materials.

In addition, in the steps of the method, cellulose microfibrils are less likely to be cut by aldehyde groups. Thus, the hydrophilized cellulose fibers obtained by the method have improved moisture-absorption properties while maintaining almost the same level of strength as the material cellulose fibers.

These hydrophilized cellulose fibers with cellulose microfibrils in which primary hydroxy groups are oxidized to carboxy groups exhibit high heat-release effect and high exothermal effect due to their high moisture-absorption properties. Thus, the hydrophilized cellulose fibers are suitably used for various fiber products.

Examples of the fiber products include garments, miscellaneous goods, interior goods, bedclothes, industrial materials, sanitary goods, medical materials, and the like.

Examples of the garments include street clothes, sportswear, loungewear, relaxation wear, pajamas, nightclothes, underwear, office clothes, working clothes, cooking smocks, nursing lab coats, patient gown, caring clothes, school uniforms, kitchen clothes, and the like. Examples of the underwear include shirts, briefs, panties, pantyhose, tights, socks, leggings, belly-warmer ties, long pants, underpants, petticoats, and the like.

Examples of the miscellaneous goods include aprons, towels, gloves, scarfs, hats, shoes, sandals, bags, umbrellas, and the like.

Examples of the interior goods include curtains, carpets, mats, kotatsu covers, sofa covers, cushion covers, cloth covers for sofas, toilet seat covers, toilet seat mats, tablecloths, and the like.

Examples of the bedclothes include cloth covers for quilts, filling cotton for quilts, blankets, cloth covers for blankets, pillow fillings, sheets, waterproof sheets, quilt covers, pillowcases, and the like.

Examples of the industrial materials include filters and the like.

Examples of the sanitary good and medical material include hemostatic materials, cottons, sponges, gauzes, masks, bandages, supporters, and the like.

The hydrophilized cellulose fibers of the present invention are especially suitably used as hemostatic materials such as hemostatic gauzes.

Such hemostatic materials enable prompt and reliable hemostasis in a short period of time even in the case of serious bleeding. Moreover, a residual hemostatic material can be easily removed with tweezers, forceps, and the like after the completion of the hemostasis by blood clotting. In addition, the hemostatic materials exhibit sufficient hemostasis effect without causing rebleeding from the same site.

In the case of using the hydrophilized cellulose fibers of the present invention as a hemostatic material, the fibers may be in the form of a knitted fabric, a woven fabric, a non-woven fabric, and the like. Particularly, the fibers are preferably in the form of a knitted fabric.

In the case of the hydrophilized cellulose fibers of the present invention are in the form of a knitted fabric, carboxy groups are introduced to the inside of the fibers, and this facilitates retention of the shape of the fibers even if the carboxy groups are introduced at high density. In the case of non-woven fabrics, gauzes (woven), sponges, paper, and the like, fibers are strongly bonded one another due to the introduced carboxy groups, and thereby rigidity is increased, causing a decrease in handleability. In contrast, in the case of the knitted fabric, the hemostatic material does not suffer such disadvantages.

Use of the knitted fabric, which is excellent in stretching properties, enables processing in a stretched state, providing a flexible hemostatic material having good adhesiveness. This results in improvement in the handleability. As compared with the case of a non-woven fabric or gauze (woven), carboxy groups are introduced to the inside of the fibers, and this facilitates retention of the shape of the fibers even if the carboxy groups are introduced at a high density.

EXAMPLES

In the following, the present invention is described in more detail based on, but not limited to, examples.

Example 1

Step (1a)

According to the following process, a cloth (cellulose fibers) was oxidized with 2,2,6,6-tetramethylpiperidine-N-oxyl (hereinafter, also referred to as TEMPO) and sodium hypochlorite (NaClO) using the reaction solution and reaction conditions shown in Table 1. The cloth used was a 100% cotton knitted cloth (unbleached circular rib cloth knitted with a cotton yarn having a yarn count of 40).

TEMPO and Glauber's salt shown in Table 1 were dissolved in water, and the cloth was sufficiently immersed in the resulting solution. Then, a 5 wt % aqueous solution of NaClO was added to the solution to which the cloth was immersed. The pH of the solution was adjusted to that shown in Table 1 by adding a 1.0 M aqueous solution of HCl. The cloth was oxidized for 10 minutes under the conditions shown in Table 1 while adjusting the pH by adding a 1.0 M aqueous solution of NaOH.

TABLE 1

| Step (1a) | Reaction solution | TEMPO [2.5% owf (0.8 g/L)] Glauber's salt [13.5% owf (4.5 g/L)] NaClO (a 5 wt % aqueous solution) [135% owf (45 g/L)] |
| --- | --- | --- |
| | Reaction temperature | 25° C. |
| | Reaction time | 10 minutes |
| | pH | 10 |
| | Bath ratio (cloth:reaction solution) | 1:30 (w/w) |
| Step (2) | Reaction solution | $NaClO_2$ (a 25 wt % aqueous solution) [20% owf (10 g/L)] CG 1000 [2% owf (1 g/L)] |
| | Reaction temperature | 80° C. |
| | Reaction time | 90 minutes |
| | pH | 3.8 |
| | Bath ratio (cloth:reaction solution) | 1:20 (w/w) |
| Step (3) | Reaction solution | $H_2O_2$ (a 35 wt % aqueous solution) [5% owf (1.7 g/L)] PLC7000 [1.2% owf (0.4 g/L)] |
| | Reaction temperature | 70° C. |
| | Reaction time | 20 minutes |
| | pH | 10.6 |
| | Bath ratio (cloth:reaction solution) | 1:30 (w/w) |
| Step (4) | Reaction solution | $NaBH_4$ [4% owf (1.3 g/L)] |
| | Reaction temperature | 25° C. |
| | Reaction time | 20 minutes |
| | pH | 10.5 |
| | Bath ratio (cloth:reaction solution) | 1:30 (w/w) |

After the oxidation treatment with TEMPO and NaClO, the sample was taken out of the reaction solution and then water-washed.

Step (2)

After the oxidation treatment of step (1a), the water-washed sample cloth was further oxidized with sodium chlorite ($NaClO_2$) using the reaction solution and the conditions shown in Table 1. CG 1000 in Table 1 is a chelating agent for chlorous bleaching (NEOCRYSTAL (produced by Nicca chemical Co., Ltd.)). $NaClO_2$ was used in the form of a 25 wt % aqueous solution.

After performing the oxidation treatment of step (2) using the reaction solution and reaction conditions shown in Table 1, the sample was taken out, then washed with hot water at 60° C., and then further water-washed.

Dechlorination Treatment (Step (3))

After the oxidation treatment of step (2), hot-water washing, and water-washing, the sample cloth was dechlorinated with hydrogen peroxide ($H_2O_2$) using the reaction solution and conditions shown in Table 1. PLC7000 in Table 1 is a polycarboxylic acid-based chelating agent (NEORATE (produced by Nicca chemical Co., Ltd.)). $H_2O_2$ was used in the form of a 35 wt % aqueous solution.

After the dechlorination treatment, the sample was taken out, washed with hot water at 60° C., and then further water-washed.

Reduction Treatment (Step (4))

After the dechlorination treatment, hot-water washing, and water-washing, the sample cloth was reduced using the reaction solution and conditions shown in Table 1.

After the reduction step, the sample was taken out and then water-washed.

Neutralization Treatment

After the reduction treatment (step (4)), the sample cloth was neutralized with a 10% aqueous solution of acetic acid so that the pH was 4.

Washing and Drying Treatments

The neutralized sample cloth was water-washed (5 min×2 times). Thereafter, the sample cloth was dried in a dry room at 40° C.

Example 2

An oxidation treatment was performed in the same manner as in step (1a) in Example 1. After the oxidation treatment of step (1a), the cloth (cellulose fibers) was taken out. Thereafter, a 5 wt % aqueous solution of NaClO (135% owf (45 g/L)) was additionally added to the used reaction solution, and then another cloth (cellulose fibers) (a 100% cotton knitted cloth (unbleached circular rib cloth knitted with a cotton yarn having a yarn count of 40)) was placed in the reaction solution. The cloth was oxidized at a bath ratio of cloth:reaction solution=1:30 (weight ratio) under the same reaction conditions as in step (1a) in Example 1 (step (1b)).

The subsequent steps were performed in the same manner as in Example 1 to provide a sample.

Example 3

Oxidation treatments were performed in the same manner as in steps (1a) and (1b) in Example 2. After the oxidation treatment of step (1b), the cloth (cellulose fibers) was taken out. Thereafter, a 5 wt % aqueous solution of NaClO (135% owf (45 g/L)) was additionally added to the used reaction solution, and then another cloth (cellulose fibers) (a 100% cotton knitted cloth (unbleached circular rib cloth knitted with a cotton yarn having a yarn count of 40)) was placed in the reaction solution. The cloth was oxidized at a bath ratio of cloth:reaction solution=1:30 (weight ratio) under the same reaction conditions as in step (1a) in Example 1.

The subsequent steps were performed in the same manner as in Example 1 to provide a sample.

Example 4

Oxidation treatments were performed in the same manner as in Example 3. After the oxidation treatments, the cloth (cellulose fibers) was taken out. Thereafter, a 5 wt % aqueous solution of NaClO (135% owf (45 g/L)) was additionally added to the used reaction solution, and then another cloth (cellulose fibers) (a 100% cotton knitted cloth (unbleached circular rib cloth knitted with a cotton yarn having a yarn count of 40)) was placed in the reaction solution. The cloth was oxidized at a bath ratio of cloth:reaction solution=1:30 (weight ratio) under the same reaction conditions as in step (1a) in Example 1.

The subsequent steps were performed in the same manner as in Example 1 to provide a sample.

Example 5

Oxidation treatments were performed in the same manner as in Example 4. After the oxidation treatments, the cloth (cellulose fibers) was taken out. Thereafter, a 5 wt % aqueous solution of NaClO (135% owf (45 g/L)) was additionally added to the used reaction solution, and then another cloth (cellulose fibers) (a 100% cotton knitted cloth (unbleached circular rib cloth knitted with a cotton yarn having a yarn count of 40)) was placed in the reaction solution. The cloth was oxidized at a bath ratio of cloth:reaction solution=1:30 (weight ratio) under the same reaction conditions as in step (1a) in Example 1.

The subsequent steps were performed in the same manner as in Example 1 to provide a sample.

<Evaluation Result>

Table 2 shows the amount of carboxy groups (the amount of COOH groups), polymerization degree, and reaction efficiency of the sample cloths (Examples 1 to 5) prepared in the production steps.

The amount of carboxy groups was measured with conductometric titration.

The polymerization degree was measured in accordance with the following method.

Fibers were taken from each of the samples, and then the samples were reduced with sodium borohydride so that the residual aldehyde groups were reduced to alcohol. The fibers were dissolved in a 0.5 M solution of copper ethylenediamine, and the polymerization degree was determined by viscometry.

The copper ethylenediamine solution is alkaline. If an aldehyde group remains in the oxidized cellulose, beta elimination reaction may occur during dissolving the fibers, which may reduce the molecular weight. Therefore, the aldehyde group was previously reduced to an alcoholic hydroxy group.

The formula for determining the polymerization degree of cellulose from the vidcosity of the cellulose dissolved in the 0.5 M copper ethylenediamine solution was based on "Isogai, A., Mutoh, N., Onabe, F., Usuda, M., "Viscosity measurements of cellulose/$SO_2$-amine-dimethylsulfoxide solution", Seni Gakkaishi, 45, 299-306 (1989).".

The reaction efficiency herein means the reaction rate of the COOH group in examples determined based on the reaction rate of the COOH group in Example 1 taken as 100%.

The "unbleached cloth" in Table 2 means a cloth obtained by refining an unbleached circular rib cloth knitted with a cotton yarn having a yarn count of 40. The "bleached cotton cloth" means a cotton cloth prepared by refining an unbleached circular rib cloth knitted with a cotton yarn having a yarn count of 40, bleaching the cloth with $NaClO_2$ and $H_2O_2$ treatments, dehydrating the bleached cloth, and drying the dehydrated cloth.

Comparative Example 1

A cloth (cellulose fibers) was oxidized with TEMPO and NaClO using the reaction solution and the reaction conditions in Table 3 in the same manner as in Example 1.

The subsequent steps were performed in the same manner as in Example 1 to provide a sample.

TABLE 3

| Step (1a) | Reaction solution | TEMPO [1.7% owf (0.6 g/L)]<br>NaBr [16.5% owf (5.5 g/L)]<br>NaClO (5 wt % aqueous solution)<br>[115% owf (38 g/L)] |
|---|---|---|
| | Reaction temperature | 25° C. |
| | Reaction time | 10 minutes |
| | pH | 10 |
| | Bath ratio (cloth:reaction solution) | 1:30 (w/w) |

Comparative Example 2

An oxidation treatment was performed in the same manner as in step (1a) in Comparative Example 1. After the oxidation treatment of step (1a), the cloth (cellulose fibers) was taken out. Thereafter, a 5 wt % aqueous solution of NaClO (115% owf (38 g/L)) was additionally added to the used reaction solution, and then another cloth (cellulose fibers) (a 100% cotton knitted cloth (unbleached circular rib cloth knitted with a cotton yarn having a yarn count of 40)) was placed in the reaction solution.

The cloth was oxidized at a bath ratio of cloth:reaction solution=1:30 (weight ratio) under the same reaction conditions as in step (1a) in Comparative Example 1 (step (1b)).

The subsequent steps were performed in the same manner as in Comparative Example 1.

Comparative Example 3

Oxidation treatments were performed in the same manner as in steps (1a) and (1b) in Comparative Example 2. After the oxidation treatment of (1b), the cloth (cellulose fibers) was taken out. Thereafter, a 5 wt % aqueous solution of NaClO (115% owf (38 g/L)) was additionally added to the used reaction solution, and then another cloth (cellulose fibers) (a 100% cotton knitted cloth (unbleached circular rib cloth knitted with a cotton yarn having a yarn count of 40)) was placed in the reaction solution. The cloth was oxidized at a bath ratio

TABLE 2

| Example number | The number of oxidation steps performed (number of times) | TEMPO (% owf) | Glauber's salt (% owf) | NaClO (a 5 wt % aqueous solution) (% owf) | The amount of COOH groups (mmol/g) | Polymerization degree | Reaction efficiency (%) |
|---|---|---|---|---|---|---|---|
| Example 1 | 1 | 2.5 | 13.5 | 135 | 0.301 | 1385 | 100 |
| Example 2 | 2 | *1 | *1 | 135 | 0.356 | 1248 | 118 |
| Example 3 | 3 | *1 | *1 | 135 | 0.372 | 1222 | 124 |
| Example 4 | 4 | *1 | *1 | 135 | 0.382 | 1268 | 127 |
| Example 5 | 5 | *1 | *1 | 135 | 0.398 | 1129 | 132 |
| Unbleached cloth | — | — | — | — | — | 2510 | — |
| Bleached cotton cloth | — | — | — | — | 0.053 | 1891 | — |

*1: In the step (1b), no additional compound (e.g, TEMPO, Glauber's salt) was added and the reaction solution (containing TEMPO and Glauber's salt) used in the step (1a) was reused.

of cloth:reaction solution=1:30 (weight ratio) under the same reaction conditions as in step (1a) in Comparative Example 1.

The subsequent steps were performed in the same manner as in Comparative Example 1.

Comparative Example 4

Oxidation treatments were performed in the same manner as in Comparative Example 3. After the oxidation treatments, the cloth (cellulose fibers) was taken out. Thereafter, a 5 wt % aqueous solution of NaClO (115% owf (38 g/L)) was additionally added to the used reaction solution, and then another cloth (cellulose fibers) (a 100% cotton knitted cloth (unbleached circular rib cloth knitted with a cotton yarn having a yarn count of 40)) was placed in the reaction solution. The cloth was oxidized at a bath ratio of cloth:reaction solution=1:30 (weight ratio) under the same reaction conditions as in step (1a) in Comparative Example 1.

The subsequent steps were performed in the same manner as in Comparative Example 1.

Comparative Example 5

Oxidation treatments were performed in the same manner as in Comparative Example 4. After the oxidation treatments, the cloth (cellulose fibers) was taken out. Thereafter, a 5 wt % aqueous solution of NaClO (115% owf (38 g/L)) was additionally added to the used reaction solution, and then another cloth (cellulose fibers) (a 100% cotton knitted cloth (unbleached circular rib cloth knitted with a cotton yarn having a yarn count of 40)) was placed in the reaction solution. The cloth was oxidized at a bath ratio of cloth:reaction solution=1:30 (weight ratio) under the same reaction conditions as in step (1a) in Comparative Example 1.

The subsequent steps were performed in the same manner as in Comparative Example 1.

The "unbleached cloth" in Table 4 means a cloth obtained by refining an unbleached circular rib cloth knitted with a cotton yarn having a yarn count of 40. The "bleached cotton cloth" means a cotton cloth prepared by refining an unbleached circular rib cloth knitted with a cotton yarn having a yarn count of 40, bleaching the cloth with $NaClO_2$ and $H_2O_2$ treatments, dehydrating the bleached cloth, and drying the dehydrated cloth.

Figure 3:
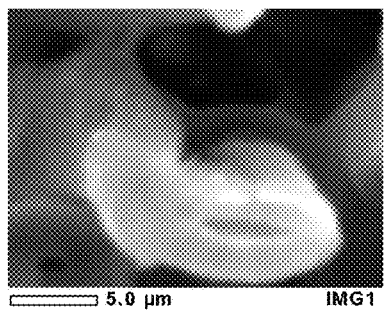
FIG. 3 is a micrograph of a cross-section of a fiber of a sample obtained in Example 1.
Figure 4:
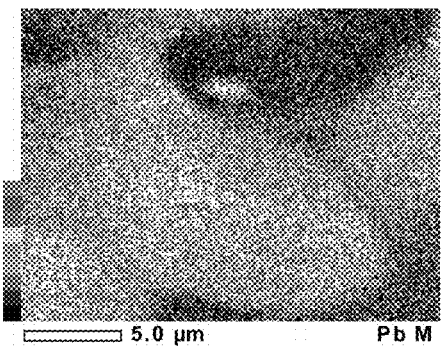
FIG. 4 is a photograph showing Pb distribution in a fiber cross-section of a sample obtained in Example 1.
Figure 5:
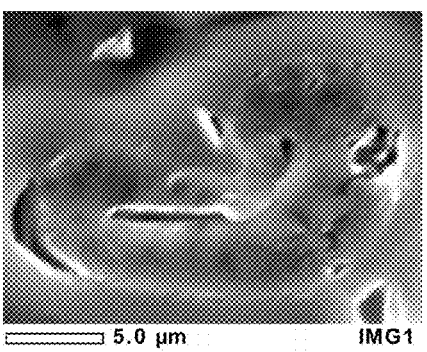
FIG. 5 is a micrograph of a cross-section of a fiber of a sample obtained in Comparative Example 1.

In addition, carboxy group distribution in a fiber cross-section of each of the samples obtained in Example 1 and Comparative Example 1 was observed. Specifically, each of the samples was immersed in ion-exchanged water, and the pH thereof was adjusted to 3 with 1N—HCl. Subsequently, the sample was treated at 25° C. for three hours, and then sufficiently washed with distilled water. Thereafter, lead (II) acetate trihydrate was added in an amount of 60 times the amount of carboxy groups contained in the sample, and the sample was treated at 25° C. for 6 hours. The treated sample was water-washed and dried. The Pb distribution in a cross-section of a fiber was then measured with SEM-EDX (JSM-6390LA: produced by JEOL Ltd.). FIG. 3 is a microgram of a cross-section of a fiber of the sample obtained in Example 1, and FIG. 4 is a photograph showing Pb distribution in a fiber cross-section of the sample obtained in Example 1. FIG. 5 is a microgram of a cross-section of a fiber of the sample obtained in Comparative Example 1, and FIG. 6 is a photograph showing Pb distribution in a fiber cross-section of the sample obtained in Comparative Example 1.

Figure 6:
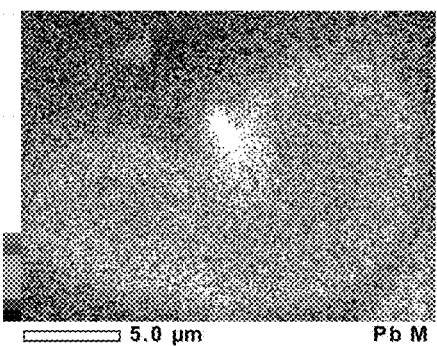
FIG. 6 is a photograph of Pb distribution in a fiber cross-section of a sample obtained in Comparative Example 1.

In FIGS. 4 and 6, the colors shown at the lower left indicate Pb concentration. A color closer to the upper side indicates a higher Pb concentration.

FIGS. 4 and 6 reveal that the sample obtained in Example 1 has a high Pb concentration in the inside of the fibers as compared with the sample obtained in Comparative Example 1.

TABLE 4

| Example number | The number of oxidation steps performed (number of times) | TEMPO (% owf) | NaBr (% owf) | NaClO (a 5 wt % aqueous solution) (% owf) | The amount of COOH groups (mmol/g) | Polymerization degree | Reaction efficiency (%) |
| --- | --- | --- | --- | --- | --- | --- | --- |
| Comparative Example 1 | 1 | 1.7 | 16.5 | 115 | 0.231 | 1392 | 100 |
| Comparative Example 2 | 2 | *2 | *2 | 115 | 0.219 | 1245 | 94.8 |
| Comparative Example 3 | 3 | *2 | *2 | 115 | 0.213 | 1233 | 92.3 |
| Comparative Example 4 | 4 | *2 | *2 | 115 | 0.188 | 1231 | 81.4 |
| Comparative Example 5 | 5 | *2 | *2 | 115 | 0.145 | 1147 | 62.6 |
| Unbleached cloth | — | — | — | — | — | 2529 | — |
| Bleached cotton cloth | — | — | — | — | 0.042 | 1883 | — |

*2: In the step (1b), no additional compound (e.g., TEMPO, NaBr) was added, and the reaction solution (containing TEMPO and NaBr) used in the step (1a) was reused.

<Evaluation Result>

Table 4 shows the amount of carboxy groups (the amount of COOH groups), the polymerization degree, and the reaction efficiency of the sample cloths (Comparative Examples 1 to 5) prepared in the above production steps.

The amount of carboxy groups, the polymerization degree, and the reaction efficiency were measured in the same manner as described above.

FIG. 1 shows a graph plotting the relation between the number of oxidation steps performed and the reaction efficiency. In FIG. 1, the number of oxidation treatments performed is shown on the abscissa axis, and the reaction efficiency is shown on the ordinate axis. In FIG. 1, values obtained when Glauber's salt was used as a co-catalyst are plotted with "■", and values obtained when NaBr was used as a co-catalyst are plotted with "◆".

Result and Review

In Comparative Examples 1 to 5, in which NaBr was used as a co-catalyst in step (1a) for oxidizing cellulose fibers with TEMPO and NaClO, as the number of reuses the reaction solution increased, the reaction efficiency decreased, as shown in Table 4 and FIG. 1.

This is presumably because NaCl produced due to consumption of NaClO inhibited the reaction of NaBr, a co-catalyst. In addition, since NaClO was added every time the reaction solution was reused, an increased amount of NaCl was produced. This presumably caused significant inhibition of the TEMPO oxidation.

On the contrary, in Examples 1 to 5, in which sodium sulfate (Glauber's salt) was used as a co-catalyst in step (1a) for oxidizing cellulose fibers with TEMPO and NaClO, as the number of reuses of the reaction solution increased, the reaction efficiency increased, as shown in Table 2 and FIG. 1.

This is presumably because the reaction of added co-catalyst was not inhibited by NaCl that was a by-product, and thus the cellulose fibers were smoothly oxidized. In addition, due to the use of sodium sulfate (Glauber's salt) as a co-catalyst, NaCl that was a by-product showed substantially no inhibiting effect on the oxidation reaction. Thereby, hydroxy groups in the cellulose fibers were efficiently oxidized to carboxy groups with NaClO added every time the reaction solution was reused. This presumably contributed to an increase in the reaction efficiency of the cellulose fibers.

Example 6

A cloth (cellulose fibers) was oxidized with TEMPO and sodium dichloroisocyanurate (SDIC) using the reaction solution and the reaction conditions shown in Table 5 in the same manner as in Example 1. The subsequent steps were performed in the same manner as in Example 1 to provide a sample.

TABLE 5

| Step (1a) | Reaction solution | TEMPO [2.5% owf (0.8 g/L)]<br>Glauber's salt [13.5% owf (4.5 g/L)]<br>SDIC [10% owf (3.3 g/L)] |
|---|---|---|
| | Reaction temperature | 25° C. |
| | Reaction time | 10 minutes |
| | pH | 10 |
| | Bath ratio<br>(cloth:reaction<br>solution) | 1:30 (w/w) |

Example 7

An oxidation treatment was performed in the same manner as in step (1a) in Example 6. After the oxidation treatment of step (1a), the cloth (cellulose fibers) was taken out. Thereafter, 10% owf (3.3 g/L) of SDIC was additionally added to the used reaction solution, and then another cloth (cellulose fibers) (a 100% cotton knitted cloth (unbleached circular rib cloth knitted with a cotton yarn having a yarn count of 40)) was placed in the reaction solution. The cloth was oxidized at a bath ratio of cloth:reaction solution=1:30 (weight ratio) under the same reaction conditions as in step (1a) in Example 6 (step (1b)).

The subsequent steps were performed in the same manner as in Example 6 to provide a sample.

Example 8

Oxidation treatments were performed in the same manner as in steps (1a) and (1b) in Example 7. After the oxidation treatment of step (1b), the cloth (cellulose fibers) was taken out. Thereafter, 10% owf (3.3 g/L) of SDIC was additionally added to the used reaction solution, and then another cloth (cellulose fibers) (a 100% cotton knitted cloth (unbleached circular rib cloth knitted with a cotton yarn having a yarn count of 40)) was placed in the reaction solution. The cloth was oxidized at a bath ratio of cloth:reaction solution=1:30 (weight ratio) under the same reaction conditions as in step (1a) in Example 6.

The subsequent steps were performed in the same manner as in Example 6 to provide a sample.

Example 9

Oxidation treatments were performed in the same manner as in Example 8. After the oxidation treatments, the cloth (cellulose fibers) was taken out. Thereafter, 10% owf (3.3 g/L) of SDIC was additionally added to the used reaction solution, and then another cloth (cellulose fibers) (a 100% cotton knitted cloth (unbleached circular rib cloth knitted with a cotton yarn having a yarn count of 40)) was placed in the reaction solution. The cloth was oxidized at a bath ratio of cloth:reaction solution=1:30 (weight ratio) under the same reaction conditions as in step (1a) in Example 6.

The subsequent steps were performed in the same manner as in Example 6 to provide a sample.

Example 10

Oxidation treatments were performed in the same manner as in Example 9. After the oxidation treatments, the cloth (cellulose fibers) was taken out. Thereafter, 10% owf (3.3 g/L) of SDIC was additionally added to the used reaction solution, and then another cloth (cellulose fibers) (a 100% cotton knitted cloth (unbleached circular rib cloth knitted with a cotton yarn having a yarn count of 40)) was placed in the reaction solution. The cloth was oxidized at a bath ratio of cloth:reaction solution=1:30 (weight ratio) under the same reaction conditions as in step (1a) in Example 6.

The subsequent steps were performed in the same manner as in Example 6 to provide a sample.

<Evaluation Result>

Table 6 shows the amount of carboxy groups (the amount of COOH groups), the polymerization degree, loss in whiteness, and the reaction efficiency of the sample cloths (Examples 6 to 10) prepared in the above production steps.

The amount of carboxy groups, the polymerization degree, and the reaction efficiency were measured in the same manner as described above.

The loss of whiteness was determined by calculating whiteness (using Macbeth WHITE-EYE 3000 produced by Kollmorgen Instruments Corporation measured in a micro area) of the sample before and after drying with the formula L*-3b* based on CIELAB color coordinate system, and measuring the difference therebetween. The absolute dry whiteness means whiteness after the absolute dry weight is measured in accordance with "JIS L-0105 4.3".

The "unbleached cloth" in Table 6 means a cloth obtained by refining an unbleached circular rib cloth knitted with a cotton yarn having a yarn count of 40. The "bleached cotton cloth" means a cotton cloth prepared by refining an unbleached circular rib cloth knitted with a cotton yarn having a yarn count of 40, bleaching the cloth with $NaClO_2$ and $H_2O_2$ treatments, dehydrating the bleached cloth, and drying the dehydrated cloth.

TABLE 6

| Example number | The number of oxidation steps performed (number of times) | TEMPO (% owf) | Glauber's salt (% owf) | SDIC (% owf) | The amount of COOH groups (mmol/g) | Polymerization degree | Loss in whiteness | Reaction efficiency (%) |
|---|---|---|---|---|---|---|---|---|
| Example 6 | 1 | 2.5 | 13.5 | 10 | 0.302 | 1398 | −0.5 | 100 |
| Example 7 | 2 | *3 | *3 | 10 | 0.318 | 1200 | −0.8 | 105 |
| Example 8 | 3 | *3 | *3 | 10 | 0.326 | 1055 | −0.7 | 108 |
| Example 9 | 4 | *3 | *3 | 10 | 0.328 | 966 | −0.7 | 109 |
| Example 10 | 5 | *3 | *3 | 10 | 0.348 | 905 | −0.5 | 115 |
| Unbleached cloth | — | — | — | — | — | 2387 | — | — |
| Bleached cotton cloth | — | — | — | — | 0.052 | 1892 | — | — |

*3: In the step (1b), no additional compound (e.g., TEMPO, Glauber's salt) was added, and the reaction solution (containing TEMPO and Glauber's salt) used in the step (1a) was reused.

Result and Review

Table 6 shows that also in the case of oxidizing cellulose fibers with TEMPO and SDIC using sodium sulfate (Glauber's salt) as a co-catalyst in step (1a), the reaction efficiency increased as the number of reuses of the reaction solution increased, as well as Example 1 to 5, in which NaClO was used.

Thus, it is found that in the case of reusing the reaction solution used in step (1a), SDIC can also be used as an oxidizing agent.

Example 11

Step (1a)

A cloth (cellulose fibers) was oxidized with 2,2,6,6-tetramethylpiperidine-N-oxyl (hereinafter, also referred to as TEMPO) and sodium hypochlorite (NaClO) by the following process using the reaction solution and reaction conditions shown in Table 7. The cloth used was a rayon cloth (1×1 rib knit structure as a base structure, knitted with a yarn having a rayon count of 40 and a circular rib knitting machine (about 33.3 cm, 870 N).

TEMPO and Glauber's salt shown in Table 7 were dissolved in water, and then the cloth was sufficiently immersed in the resulting solution. A 5 wt % aqueous solution of NaClO was additionally added to the solution with the cloth immersed therein. The pH of the solution was adjusted with a 1.0 M aqueous solution of HCL so that the pH shown in Table 10 was achieved. The cloth was oxidized under the conditions shown in Table 7 for 10 minutes while controlling pH with the 1.0 M aqueous solution of NaOH.

After the oxidation treatment with TEMPO and NaClO, the sample was taken out of the reaction solution, and then water-washed.

TABLE 7

| Step (1a) | Reaction solution | TEMPO [5% owf (0.25 g/L)] |
| | | Glauber's salt [27% owf (2.7 g/L)] |
| | | NaClO (a 5 wt % aqueous solution) [678% owf (67.8 g/L)] |
| | Reaction temperature | 25° C. |
| | Reaction time | 4 hours |
| | pH | 10 |
| | Bath ratio (cloth:reaction solution) | 1:100 (w/w) |
| Step (2) | Reaction solution | NaClO$_2$ (a 25 wt % aqueous solution) [20% owf (10 g/L)] |
| | | CG 1000 [2% owf (1 g/L)] |
| | Reaction temperature | 80° C. |
| | Reaction time | 60 minutes |
| | pH | 3.75 |
| | Bath ratio (cloth:reaction solution) | 1:25 (w/w) |
| Step (3) | Reaction solution | H$_2$O$_2$ (a 35 wt % aqueous solution) [10% owf (3.3 g/L)] |
| | | PLC7000 [1.2% owf (0.4 g/L)] |
| | Reaction temperature | 70° C. |
| | Reaction time | 10 minutes |
| | pH | 10.6 |
| | Bath ratio (cloth:reaction solution) | 1:30 (w/w) |

Step (2)

After the oxidation treatment of step (1a), the water-washed sample cloth was further oxidized with sodium chlorite (NaClO$_2$) using the reaction solution and the reaction conditions shown in Table 7. CG 1000 in Table 7 is a chelating agent for chlorous bleaching (NEOCRYSTAL (produced by Nicca chemical Co., Ltd.)). NaClO$_2$ was used in the form of a 25 wt % aqueous solution.

After performing the oxidation treatment of step (2) using the reaction solution and the reaction conditions shown in Table 7, the sample was taken out, then washed with hot water at 60° C., and then further water-washed.

Dechlorination Treatment (Step (3))

The sample cloth that was washed with hot water and water after the oxidation treatment of step (2) was dechlorinated with hydrogen peroxide (H$_2$O$_2$) using the reaction solution shown in Table 7. PLC7000 in Table 7 is a polycarboxylic acid-based chelating agent (NEORATE (produced by Nicca chemical Co., Ltd.)). H$_2$O$_2$ was used in the form of a 35 wt % aqueous solution.

After the dechlorination treatment, the sample was taken out, then washed with hot water at 60° C., and then further water-washed. The subsequent steps were performed in the same manner as in Example 1 to provide a sample.

Example 12

A sample was obtained in the same manner as in step (1a) in Example 11, except that the condition "NaClO (a 5 wt % aqueous solution) [678% owf (67.8 g/L)]" was changed to "NaClO (a 5 wt % aqueous solution) [783% owf (78.3 g/L)]".

Example 13

A 100% cotton knitted cloth (unbleached circular rib cloth knitted with a cotton yarn having a yarn count of 40) was mercerized using the solution and the conditions shown in Table 8.

The mercerized cotton cloth was subjected to steps (1a), (2), and (3) in the same manner as in Example 1 using the reaction solutions and the reaction conditions shown in Table 8. The subsequent steps were performed in the same manner as in Example 1 to provide a sample.

TABLE 8

| Mercerization | Solution used | A NaOH aqueous solution [21%] |
|---|---|---|
| | Reaction temperature | 20° C. |
| | Reaction time | 4 hours |
| | Bath ratio (cloth:reaction solution) | 1:10 (w/w) |
| Step (1a) | Reaction solution | TEMPO [5% owf (0.25 g/L)] Glauber's salt [27% owf (2.7 g/L)] NaClO (a 5 wt % aqueous solution) [783% owf (78.3 g/L)] |
| | Reaction temperature | 25° C. |
| | Reaction time | 2 hours |
| | pH | 10 |
| | Bath ratio (cloth:reaction solution) | 1:100 (w/w) |
| Step (2) | Reaction solution | NaClO$_2$ (a 25 wt % aqueous solution) [20% owf (8 g/L)] CG 1000 [2% owf (1 g/L)] |

Example 14

A sample was obtained in the same manner as in Example 13 except that the reaction time in step (1a) was 4 hours.

Comparative Example 6

A knitted cloth (Surgicel (registered trademark) produced by Johnson & Johnson K.K) made of oxidized regenerated cellulose (ORC) oxidized with nitrogen dioxide was used as a sample.

<Evaluation Result>

Table 9 shows the amount of carboxy groups (the amount of COOH groups) and the polymerization degree of the sample cloths (Examples 11 to 14 and Comparative Example 6) prepared in the above production steps.

The amount of carboxy groups and the polymerization degree were measured in the same manner as described above.

"Unbleached rayon cloth" in Table 9 means a cloth obtained by refining an unbleached cloth (1×1 rib knit structure as a base structure, knitted with a thread having a rayon count of 40 using a circular rib knitting machine (about 33.3 cm, 870 N). "Unbleached cotton cloth" means a cloth obtained by refining an unbleached circular rib cotton cloth knitted with a cotton yarn having a yarn count of 40.

TABLE 9

| Example number | TEMPO (% owf) | Glauber's salt (% owf) | NaClO (a 5 wt % aqueous solution) (% owf) | The amount of COOH groups (mmol/g) | Polymerization degree | pH | Hemostatic properties | | | Handleability | |
|---|---|---|---|---|---|---|---|---|---|---|---|
| | | | | | | | Blood Absorption | Blood clotting | Field test | Flexibility | Adhesiveness |
| Example 11 | 5 | 27 | 678 | 1.95 | 120 | 6.5 | ○ | ○ | ○ | 6.2 | ○ |
| Example 12 | 5 | 27 | 783 | 2.25 | 105 | 6.8 | ○ | ○ | ○ | 4.1 | ○ |
| Comparative Example 6 | — | — | — | 2.02 | 60 | 1.5 | ○ | ○ | X | 6.1 | ○ |
| Unbleached rayon cloth | — | — | — | 0.05 | 382 | 7.0 | ○ | X | X | 8.5 | X |
| Example 13 | 5 | 27 | 783 | 1.73 | 127 | 6.8 | ○ | ○ | ○ | 3.5 | ○ |
| Example 14 | 5 | 27 | 783 | 2.05 | 105 | 6.8 | ○ | ○ | ○ | 3.1 | ○ |
| Unbleached cotton cloth | — | — | — | 0.05 | 740 | 6.5 | X | X | X | 6.4 | — |

TABLE 8-continued

| | Reaction temperature | 80° C. |
|---|---|---|
| | Reaction time | 60 minutes |
| | pH | 3.75 |
| | Bath ratio (cloth:reaction solution) | 1:25 (w/w) |
| Step (3) | Reaction solution | H$_2$O$_2$ (a 35 wt % aqueous solution) [10% owf (3.3 g/L)] PLC7000 [1.2% owf (0.4 g/L)] |
| | Reaction temperature | 70° C. |
| | Reaction time | 10 minutes |
| | pH | 10.6 |
| | Bath ratio (cloth:reaction solution) | 1:30 (w/w) |

<Evaluation of Hemostatic Properties>

(1) Blood Absorption Test

Each sample was cut into a strip (length 4 cm×width 1 cm). The lower end (0.1 cm) of each of the samples was immersed in experimental animal blood for 1 minute and observed. The sample in which the experimental animal blood penetrated to 0.5 cm or higher from the lower end of the sample was evaluated as "○". The sample in which penetration of blood to 0.5 cm or higher was not observed was evaluated as "x".

(2) Blood Clotting Properties Test

In the blood absorption test, clotting state of the blood absorbed in each sample was observed. The sample in which blood clotting was observed was evaluated as "○". The sample in which no blood clotting was observed was evaluated as "x".

(3) Hemostasis Field Test

Each sample was cut into a sample piece (1×1 cm). The sample piece was applied to a bleeding portion with blood oozing out therefrom, and then gauze was pressed against the portion. The sample was left to stand for 2 minutes, and then was peeled off. In the case that the portion was completely free of bleeding after the peeling, the sample was evaluated as "○". In the case that the portion was still bleeding after the peeling, the sample was evaluated as "x".

<Handleability Evaluation>

In order to evaluate the shape of bleeding portions, each sample was evaluated for feel and adhesiveness.

The feel was determined by measuring "flexibility" with Kawabata Evaluation System (KES) measuring apparatus (KATO TECH Co., Ltd.), which is commonly used as a feel measuring system.

The adhesiveness was evaluated by the method actually used in surgery. Specifically, a sample piece (1×1 cm) was cut out of each of the samples with scissors and applied to a bleeding portion, and then shear stress was applied to the bleeding portion to evaluate the adhesiveness. The sample piece which was not peeled off by the shear stress was evaluated as "○". The sample which was peeled off was evaluated as "x".

INDUSTRIAL APPLICABILITY

According to the present invention, a hydrophilized cellulose fiber producing method comprising the step of oxidation of a part of hydroxy groups in cellulose fibers to carboxy groups is provided. According to the present invention, a hemostatic material having excellent hemostatic effect is also provided.

The invention claimed is:

1. A method of reusing a reaction solution, comprising steps of:
    oxidizing cellulose fibers in a reaction solution comprising a N-oxyl compound, an oxidizing agent, and sodium sulfate so as to provide oxidized cellulose fibers; and
    separating the oxidized cellulose fibers from the reaction solution used in the oxidizing step, and then adding other cellulose fibers and an oxidizing agent in the reaction solution so as to oxidize the added cellulose fibers.

2. A hydrophilized cellulose fiber producing method, comprising steps of:
    (1a) oxidizing cellulose fibers in a reaction solution comprising a N-oxyl compound, an oxidizing agent, and sodium sulfate so as to provide first oxidized cellulose fibers; and
    (1b) separating the first oxidized cellulose fibers obtained in the step (1a) from the reaction solution, and then adding other cellulose fibers and an oxidizing agent to the reaction solution so as to oxidize the added cellulose fibers and to provide second oxidized cellulose fibers,
    wherein the oxidizing agent used in at least one step selected from the group consisting of the step (1a) and the step (1b) is a halogen acid oxidizing agent, and
    if the halogen acid oxidizing agent is used in the step (1b), the halogen acid oxidizing agent is a hypohalous acid, a halogenated isocyanuric acid, or a salt thereof.

3. The method according to claim 2,
    wherein the N-oxyl compound used in the step (1a) is 2,2,6,6-tetramethylpiperidine-N-oxyl.

4. The method according to claim 2,
    wherein the cellulose fibers used in the step (1a) are rayon fibers.

5. The method according to claim 2,
    wherein the step (1b) is performed twice or more.

6. The method according to claim 2, further comprising step (2) of oxidizing the first oxidized cellulose fibers obtained in the step (1a) and the second oxidized cellulose fibers obtained in the step (1b) in a reaction solution comprising an oxidizing agent.

7. The method according to claim 1, wherein in the step (1b), the reaction solution is used in a bath ratio in a range from 10 to 100 g relative to one gram of the added cellulose fibers.

8. The method according to claim 6, wherein the oxidizing agent used in the step (2) is a halogen acid oxidizing agent.

9. The method according to claim 8,
    wherein the halogen acid oxidizing agent used in the step (2) is a halous acid or a salt thereof.

10. The method according to claim 6, further comprising step (3) of dehalogenating the oxidized cellulose fibers obtained in the step (2) with a dehalogenating agent.

11. The method according to claim 10, further comprising step (4b) of reducing the oxidized cellulose fibers obtained in the step (3) in a reaction solution comprising a reducing agent.

12. The method according to claim 10,
    wherein the dehalogenating agent is at least one material selected from the group consisting of hydrogen peroxide and ozone.

13. The method according to claim 6, further comprising step (4a) of reducing the oxidized cellulose fibers obtained in the step (2) in a reaction solution comprising a reducing agent.

14. The method according to claim 13,
    wherein the reducing agent is at least one material selected from the group consisting of thiourea, hydrosulfite, sodium bisulfite, sodium borohydride, sodium cyanoborohydride, and lithium borohydride.

15. The method according to claim 6, further comprising a step of mixing the oxidized cellulose fibers obtained in the step (2) with a dehalogenating agent and a reducing agent so as to perform a dehalogenation treatment that removes halogens remaining in the oxidized cellulose fibers simultaneously with a reduction treatment that reduces ketone group in at least one position selected from the group consisting of the 2-position and 3-position of a glucose unit in the oxidized cellulose fibers.

* * * * *